US00PP07975P

United States Patent [19]

Bradford et al.

[11] Patent Number: Plant 7,975

[45] Date of Patent: Sep. 15, 1992

[54] PLUM TREE (RED NOBLE)

[76] Inventors: Lowell G. Bradford, 12439 E. Savana Rd.; Norman G. Bradford, 11875 E. Savana Rd., both of Le Grand, Calif. 95333

[21] Appl. No.: 684,855

[22] Filed: Apr. 15, 1991

[51] Int. Cl.[5] ..... A01H 5/00
[52] U.S. Cl. ..... Plt./38.1
[58] Field of Search ..... Plt./38

[56] References Cited

U.S. PATENT DOCUMENTS

P.P. 2,539 6/1965 Anderson ..... Plt. 38

*Primary Examiner*—James R. Feyrer

[57] ABSTRACT

The present invention relates to a plum tree and more particularly to a new and distinct variety broadly characterized by a medium size, vigorous, and medium productive tree, which requires cross pollinization. The fruit matures under the ecological conditions described in late May, with first picking on May 26th, 1990, and is uniformly medium in size, clingstone in type, deep red to purplish red in skin color, attractive in shape, deliciously sweet in flavor, and exceptionally firm in texture, resulting in excellent quality for keeping and shipping. The variety was developed as an open pollinated seedling of an unnamed seedling.

1 Drawing Sheet

BACKGROUND OF THE NEW VARIETY

In a continuing effort to improve the quality of shipping fruits, we, the inventors, typically hybridize a large number of nectarine, peach, plum, apricot, and cherry seedlings each year. The present invention relates to a new and distinct variety of plum tree, which has been denominated varietally as "Red Noble". Each year we grow a large number of seeds from selected seed parents that have been hybridized by selected pollen parents. We also grow a large number of seeds from selected seed parents that were open pollinated by unknown pollen sources. The present variety was developed by us in 1984, and the resulting seedling was planted in a cultivated area of our experimental orchard at Bradford Farms near Le Grand, Calif. in Merced County (San Joaquin Valley). Specifically, this seedling was originated by growing an open pollinated seed of an unnamed seedling. Subsequent to origination of the present variety of plum tree, we asexually reproduced it by budding and grafting, and such reproduction of plant and fruit characteristics were true to the original plant in all respects.

The present variety is most similar to Red Beaut (U.S. Plant Pat. No. 2,539) by being self-sterile and by producing fruit that is early in maturing and medium in size, but is distinguished therefrom and an improvement thereon by producing fruit that is darker purplish red in color, that is clingstone rather than freestone, that is firmer in texture, and that is substantially better in flavor. The improvement in flavor of the present variety enables fruit picked immaturely to still taste very good, and the improvement in firmness allows the grower the option of shipping a tree ripened product to the market.

DRAWING

The accompanying photograph exhibits four whole fruits positioned to display the characteristics of the skin color and form; one fruit divided transversely to its axial diameter to reveal the flesh, stone, and stone cavity; and several leaves, all typical of the subject variety.

POMOLOGICAL CHARACTERISTICS

Referring now more specifically to the pomological characteristics of this new and distinct variety of plum tree, the following has been observed under the ecological conditions prevailing at the experimental orchard of the inventors near Le Grand, Merced County (San Joaquin Valley), Calif., and was developed at the state of hard eating ripe on May 28, 1990. All major color code designations are by reference to the Inter-Society Color Council, National Bureau of Standards. Common color names are also used occasionally.

TREE

Size: Medium.
Vigor: Vigorous.
Growth: Upright and dense.
Form: Vase formed.
Hardiness: Half hardy.
Production: Medium productivity.
Bearing: Regular bearer.
Trunk:
- *Size.*—Medium.
- *Texture.*—Shaggy.
- *Bark color.*—Brownish gray [64. brGy].
- *Lenticels.*—Numerous. Color: Brownish gray [64. brGy]. Size: 1/16" to ¼" [1.6–6.4 mm.].

Branches:
- *Size.*—Medium.
- *Texture.*—Smooth.
- *Color.*—1st year wood topside: Deep yellowish brown [75. deep yBr]. 1st year wood underside: Moderate yellow green [120. m.YG]. Older wood: Dark yellowish brown [78. d.yBr].
- *Lenticels.*—Numerous, very small.

Leaves:
- *Size.*—Medium. Average length: 3½" [88.9 mm.]. Average width: 1⅞" [47.6 mm.].
- *Thickness.*—Medium.
- *Form.*—Obovate.
- *Apex.*—Mucronate.
- *Base.*—Acute.

*Surface.*—Slightly rugose.

*Color.*—Dorsal surface: Dark olive green [126. d.OlG]. Ventral surface: Grayish yellow green [122. gy.YG].

*Margin.*—Finely serrate.

*Venation.*—Pinnately net veined.

*Petiole.*—Average length: 7/16" [11.1 mm.]. Average thickness: 1/16" [1.6 mm.]. Dorsal color: Light grayish red [18. l.gy.R]. Ventral color: Grayish yellow green [122. gy.YG].

*Stipules.*—Numerous. Average length: 3/16" [4.8 mm.].

*Glands.*—Numbers: Mostly 2 per leaf. Position: Mostly alternately positioned on petiole very close to base of blade. Size: Small. Form: Globose. Color: Grayish red [19. gy.R].

Flower buds:

*Hardiness.*—Half hardy.

*Size.*—Medium.

*Length.*—Medium.

*Form.*—Free.

*Surface.*—Pubescent.

Flowers:

*Blooming period.*—Early as compared with other varieties.

*Size.*—Medium.

*Color.*—White [263. White].

FRUIT

Maturity when described: Hard but eating ripe, May 28, 1990.

Date of first picking: May 26, 1990.

Date of last picking: Jun. 4, 1990.

Size: Uniform, medium.

*Average diameter axially.*—2⅛" [54.0 mm].

*Average traversely in suture plane.*—2⅛" [54.0 mm].

Form: Uniform, slightly unsymmetrical, globose to slightly obovoid.

*Longitudinal section form.*—Slightly obovate.

*Transverse section through diameter.*—Round.

Suture: A sharp crack near the base becoming an inconspicuous shallow line discontinuing at the apex, with a slight depression beyond the pistil point.

Ventral surface: Rounded with a slight hump along one side of suture.

Lips: Lipped only near the base.

Cavity: Flaring, circular, elongated in the suture plane, suture showing on one side only.

Base: Truncate, slightly cuneate.

Apex: Rounded.

Pistil point: An inconspicuous dot at the end of the suture line, not necessarily symmetrical with respect to the apex.

Stem: Medium.

*Average length.*—⅜" [9.5 mm.].

*Average width.*—3/32" [2.4 mm.].

Skin:

*Thickness.*—Thin.

*Texture.*—Medium.

*Tenacity.*—Tenacious to flesh.

*Tendency to crack.*—None observed as of yet.

*Color.*—Very dark purplish red [260. v.d.pR] over a deep red [13. deep R] background toward the shoulders with some strong orange yellow [68. s.OY] freckling more toward the apex.

Flesh:

*Color.*—Light yellow [86. l.Y] to the stone.

*Amygdalin.*—Moderate.

*Juice.*—Abundant, rich.

*Texture.*—Very firm, tough, crisp.

*Fibers.*—Abundant, fine, tender.

*Ripens.*—Almost evenly, but slightly earlier at the apex.

*Flavor.*—Very sweet with medium acidity.

*Aroma.*—Distinct.

*Eating quality.*—Outstanding, even if picked prematurely.

STONE

Type: Clingstone.

Form: Oval.

Base: Slightly oblique.

Apex: Acute.

Sides: Equal.

Surface: Rugose, with a single groove on each side of the dorsal fin.

Color: Light orange yellow [70. l.OY].

Average width: ⅝" 15.9 mm.].

Average length: 13/16" [20.6 mm.].

Average thickness: ⅜" [9.5 mm.].

Average pit wall thickness: 1/16" [1.6 mm.].

Tendency to split: Very slight.

Kernel:

*Form.*—Oval to conic.

*Taste.*—Bitter.

*Viable.*—Yes.

*Average width.*—⅜" [9.5 mm.].

*Average length.*—7/16" [11.11 mm.].

Pellicle color: Strong yellowish brown [74. s.yBr].

Amygdalin: Abundant.

USE

Market: Fresh and long distance shipping.

Keeping quality: Excellent.

Shipping quality: Excellent.

Resistance to insects: No unusual susceptibilities noted.

Resistance to diseases: No unusual susceptibilities noted.

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, substantially as illustrated and described, which most nearly resembles Red Beaut (U.S. Plant Pat. No. 2,539) by being self-sterile and by producing fruit that is early in maturing and medium in size, but is distinguished therefrom and an improvement thereon by producing fruit that is darker purplish red in color, that is clingstone rather than freestone in type, that is firmer in texture, and that is substantially better in flavor.

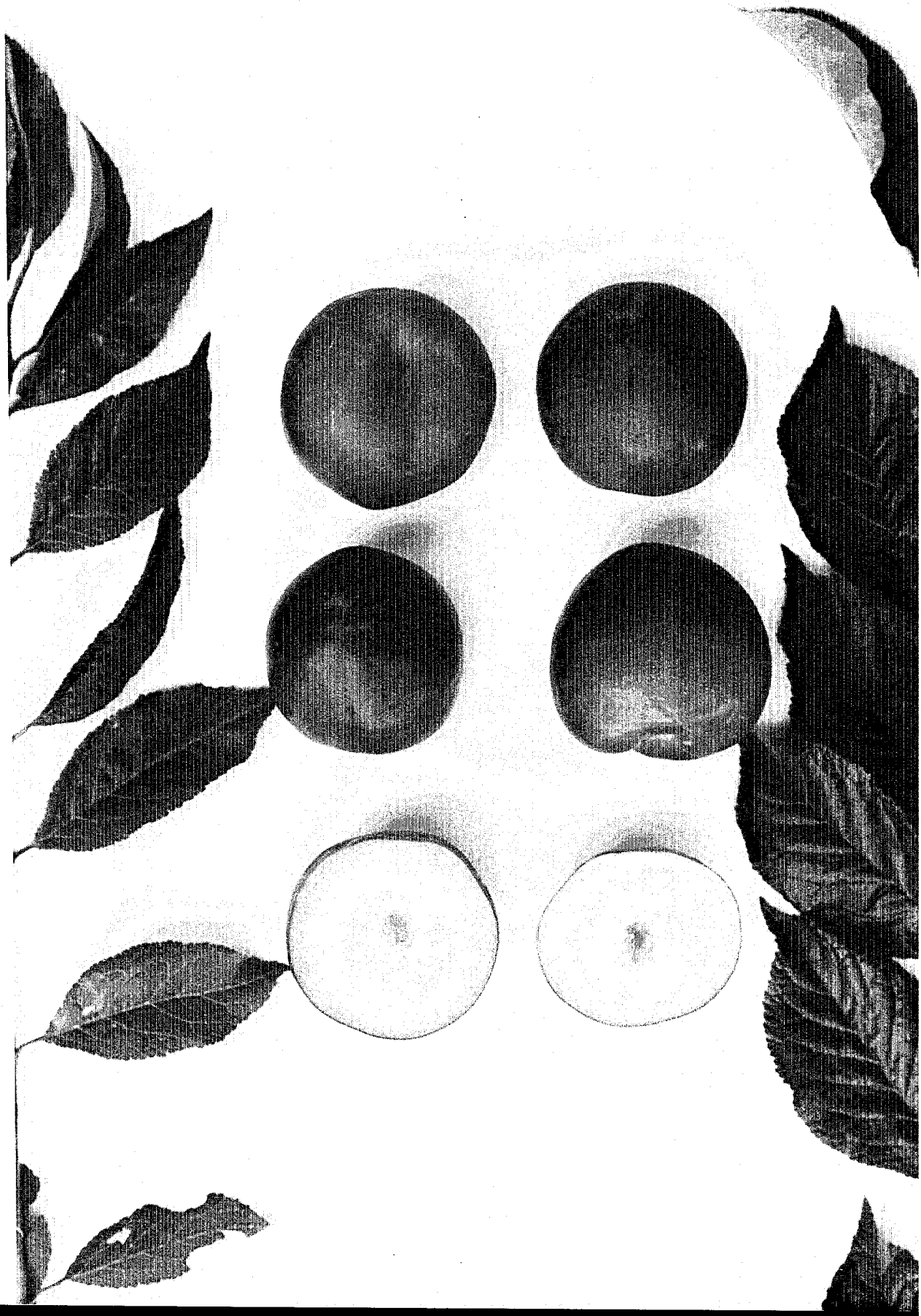

* * * * *